United States Patent
Shim

(10) Patent No.: US 12,252,468 B2
(45) Date of Patent: Mar. 18, 2025

(54) METHOD FOR PURIFYING WASTE N-METHYL-2-PYRROLIDONE MIXTURE SOLUTION

(71) Applicants: JAEWON INDUSTRIAL CO., LTD, Jeollanam-do (KR); EM Tech. CO., LTD, Chungcheongnam-do (KR)

(72) Inventor: Sung Won Shim, Jeollanam-do (KR)

(73) Assignees: JAEWON INDUSTRIAL CO., LTD, Jeollanam-do (KR); EM TECH. CO., LTD, Chungcheongnam-do (KR)

( * ) Notice: Subject to any disclaimer, the term of this patent is extended or adjusted under 35 U.S.C. 154(b) by 770 days.

(21) Appl. No.: 17/604,049

(22) PCT Filed: Jul. 7, 2020

(86) PCT No.: PCT/KR2020/008854
§ 371 (c)(1),
(2) Date: Oct. 15, 2021

(87) PCT Pub. No.: WO2021/006598
PCT Pub. Date: Jan. 14, 2021

(65) Prior Publication Data
US 2022/0144772 A1    May 12, 2022

(30) Foreign Application Priority Data
Jul. 8, 2019  (KR) .................. 10-2019-0082112

(51) Int. Cl.
*C07D 207/26*    (2006.01)
(52) U.S. Cl.
CPC .................. *C07D 207/26* (2013.01)

(58) Field of Classification Search
CPC .................................................. C07D 207/26
See application file for complete search history.

(56) References Cited

U.S. PATENT DOCUMENTS

| 2,964,535 A | 12/1960 | Clements |
| 6,051,720 A | 4/2000 | Geibel et al. |
| 2013/0150591 A1 | 6/2013 | Pinkos et al. |

FOREIGN PATENT DOCUMENTS

| KR | 10-1995-0017953 A | 7/1995 |
| KR | 10-2013-0064021 A | 6/2013 |
| KR | 10-2018-0069284 A | 6/2018 |
| WO | WO 2014/079720 A1 | 5/2014 |

OTHER PUBLICATIONS

International Search Report for PCT/KR2020/008854 mailed on Oct. 8, 2020.
Office action issued on Nov. 17, 2019 from Korean Patent Office in a counterpart Korean Patent Application No. 10-2019-0082112 (all the cited references are listed in this IDS.) (English translation is also submitted herewith.).
Notice of Allowance issued on Mar. 24, 2020 from Korean Patent Office in a counterpart Korean Patent Application No. 10-2019-0082112 (all the cited references are listed in this IDS.) (English translation is also submitted herewith.).

*Primary Examiner* — Laura L Stockton
(74) *Attorney, Agent, or Firm* — The PL Law Group, PLLC

(57) ABSTRACT

A method for purifying a waste N-methyl-2-pyrrolidone (NMP) mixed solution according to an embodiment of the present disclosure includes using a base. The base according to an embodiment may be $NaBH_4$. N-methylsuccinimide and γ-butyrolactone are simultaneously removed, and high-purity NMP can be recovered by applying a base to the waste NMP mixed solution.

4 Claims, 2 Drawing Sheets

METHOD FOR PURIFYING WASTE N-METHYL-2-PYRROLIDONE MIXTURE SOLUTION

BACKGROUND

1. Technical Field

The present invention relates to a method for purifying a N-methyl-2-pyrrolidone (hereinafter referred to as NMP) mixed solution, and in particular to a method for purifying a NMP mixed solution using a base.

2. Background Art

NMP is a low-viscosity, colorless, non-toxic organic solvent with excellent heat resistance. Because NMP is a chemically stable and highly polar solvent, it is very useful for various chemical reactions that require an inert medium.

As current environmental regulations become stricter, NMP is an eco-friendly, non-toxic product in the fields of a solvent for polymer polymerization and processing, a solvent for paint manufacture, a metal surface cleaner, a solvent for synthesis and purification of pharmaceuticals, a processing solvent for semiconductors and electronic materials, a solvent for lithium battery manufacture, and the like, and its demand is increasing.

In particular, NMP is used as a solvent for forming an active material during the preparation process of a positive electrode and a negative electrode in the process of manufacturing a secondary battery, and can be used by being contained in a binder. NMP can be used as a dispersion solvent in a mixing tank of the active material, and after formation of the electrode, it can be recovered in a vaporous form in a drying step. At this time, a waste NMP may contain about 30 wt % of water.

On the other hand, when the used waste NMP is recovered and reused in the process, not only the economic effect but also the effect of reducing the emission of environmental pollution sources is significant. Therefore, research on methods for purifying the used waste NMP to produce high-purity NMP is actively conducted.

A certain amount of GBL (γ-butyrolactone) remains in the synthesis process of NMP and GBL is not easily removed during purification by distillation since the boiling point of NMP (boiling point 202° C.) is very similar to that of the impurity GBL (boiling point 204° C.), and thus about 200~400 wtppm of GBL is contained in all NMP products.

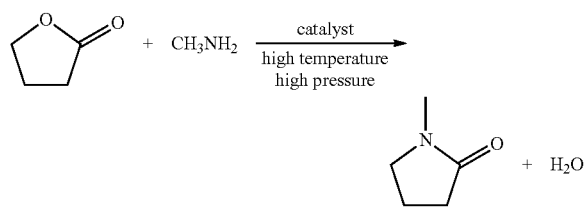

In addition, NMP is oxidized by oxygen in the air during storage, transportation and use, and a significant amount of NMS (N-methylsuccinimide, boiling point 234° C.) is produced, as a result, NMS is contained in a significant amount in NMP products and 200~500 wtppm or more of NMS may be contained in the waste NMP.

The boiling point of NMS is significantly different from that of NMP, but there is a problem that NMS is not completely removed during the purification process of the waste NMP mixed solution by distillation. In particular, since high purity NMP of 99.9 wt % or more is required in the industry used as a processing solvent for semiconductors and electronic materials and a solvent for manufacturing lithium batteries, NMS and GBL should be removed, but there is currently no solution for that.

In addition, each of 1,3-DMP (1,3-dimethyl-2-pyrrolidone) and 1,4-DMP (1,4-dimethyl-2-pyrrolidone) which are not removed by fractional distillation is usually about 300-350 wtppm in NMP products and the waste NMP mixed solution. Therefore, it is required to remove NMS and GBL in order to recover high-purity NMP after purifying the waste NMP mixed solution.

Korean Patent Laid-Open Publication No. 10-2015-0085065 discloses a method for purifying and reusing N-alkylpyrrolidone by adding a basic compound to the N-alkylpyrrolidone to be purified and then subjecting to distillation, Korean Patent Laid-Open Publication No. 10-2018-0069284 discloses a method for purifying high-purity NMP by simultaneously removing NM3P (N-methyl-3-pyrrolin-2-one) and NMS (N-methylsuccinimide) by adding a basic compound to the waste NMP mixed solution, and U.S. Pat. No. 2,964,535 discloses a method for removing GBL which is an impurity contained in NMP.

However, a method for purifying the waste NMP mixed solution by simultaneously removing impurities such as NMS (N-methylsuccinimide) and GBL (γ-butyrolactone) which are impurities present in the waste NMP mixed solution has not been proposed.

SUMMARY

The problem to be solved by the present invention is to provide a method for recovering high purity NMP by applying a fractional distillation process after simultaneously removing NMS and GBL which are impurities present in a waste NMP mixed solution.

In one embodiment, the present invention provides a method for purifying a waste NMP mixed solution that simultaneously removes NMS (N-methylsuccinimide) and GBL (gamma-butyrolactone) by adding a base to the waste NMP mixed solution, wherein NMS and GBL are by-products of NMP existing in the waste NMP mixed solution or generated in the purification process, and the base may be SBH($NaBH_4$).

In the method for purifying a waste NMP mixed solution according to another embodiment of the present invention, the SBH may be added in an amount of 0.05 to 0.10 wt % based on the total weight of the waste NMP mixed solution.

In the method for purifying a waste NMP mixed solution according to another embodiment of the present invention, moisture (water) may be added in an amount of 5 to 20 wt % based on the total weight of the total reactant, the reaction temperature may be 100 to 150° C., and the reaction time may be 10 to 60 minutes.

In the purification method of the waste NMP mixed solution according to another embodiment of the present invention, the SBH may be added after being dissolved in 10% concentration (w/v) NaOH.

According to the method for purifying a waste NMP mixed solution of the present invention, high purity NMP can be recovered by simultaneously removing NMS and GBL by applying a base.

DETAILED DESCRIPTION

Hereinafter, embodiments of the present invention will be described in detail with reference to the accompanying drawing.

In describing the constituent elements of the present invention, terms such as primary, secondary, tertiary, first, second, A, B, (a), (b) may be used. These terms are used to distinguish the constituent elements from other constituent elements, and the terms do not limit the nature, order, sequence or the like of the constituent elements. In describing the present invention, moreover, the detailed description will be omitted when a specific description for known configurations or functions incorporated herein are judged to obscure the gist of the present invention.

Unless otherwise defined, all terms in this specification are the same as the general meaning of the terms understood by those of ordinary skill in the art to which the present invention belongs, and the terms are defined as used herein in case of conflict with the meaning of terms used in the present specification. Throughout the specification, when a part "comprises" a certain component, it means that other components may be further included rather than excluding other components unless specifically stated to the contrary.

In one embodiment of one aspect, the present invention may provide a method for purifying a waste NMP mixed solution by adding a base to the waste NMP mixed solution in order to simultaneously remove NMS (N-methylsuccinimide) and GBL (gamma-butyrolactone) which are by-products of NMP contained in the waste NMP mixed solution.

Figure 1:
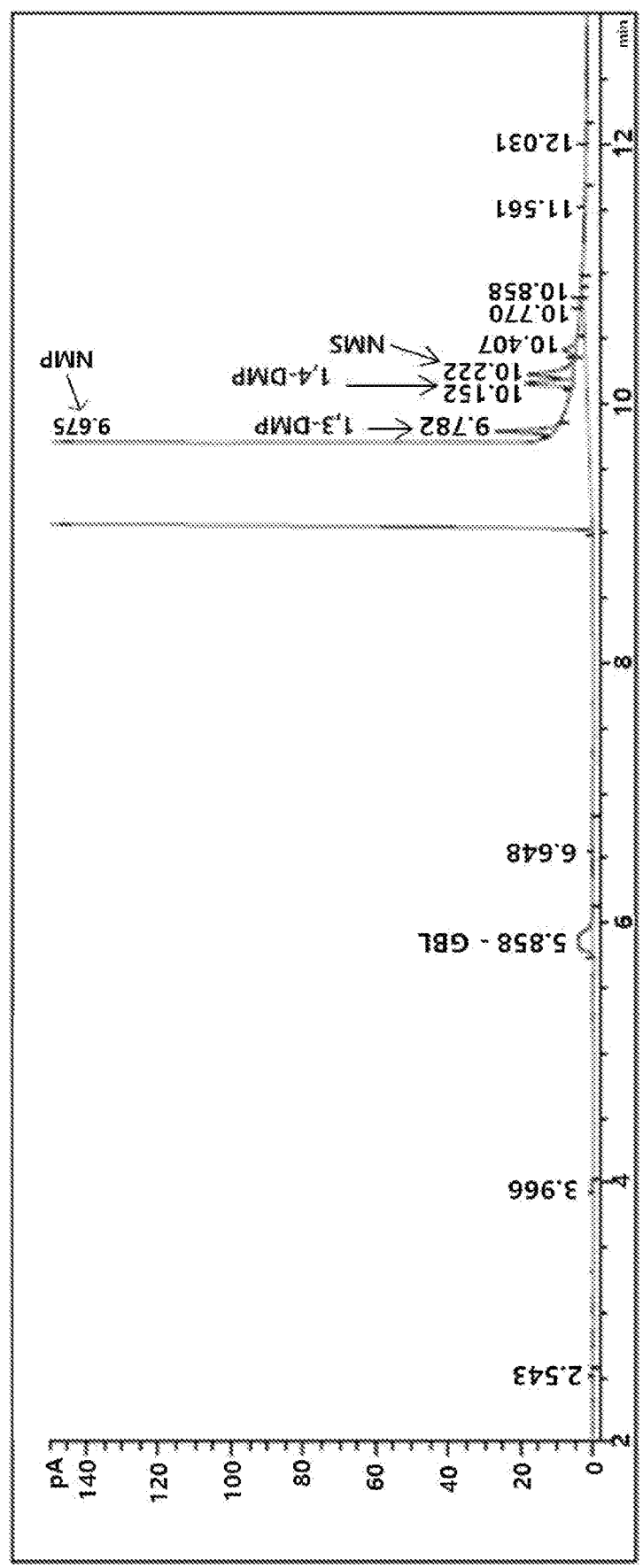
FIG. 1 shows the result of GC (Gas Chromatography) analysis of a waste NMP mixed solution containing NMS and GBL as impurities.

NMS (N-methylsuccinimide) and GBL (gamma-butyrolactone) being impurities are contained in the waste NMP mixed solution, this can be clearly seen in FIG. 1. FIG. 1 shows the result of GC (Gas Chromatography) analysis of the waste NMP mixed solution. Referring to FIG. 1, peaks are observed in NMS (N-methylsuccinimide) and GBL (gamma-butyrolactone).

According to the present invention, NMS and GBL being impurities can be completely removed at the same time by reacting a waste NMP mixed solution with a reducing agent such as SBH. That is, NMS (boiling point: 234° C.) contained in the waste NMP mixed solution reacts with SBH to be converted to 5-hydroxy-N-methyl-2-pyrrolidone (boiling point: 276° C.) as shown in Scheme 1 below, and GBL (boiling point: 204° C.) contained in the waste NMP mixed solution reacts with SBH to be converted to 1,4-butanediol (boiling point: 230° C.) as shown in Scheme 2 below.

The boiling point of NMP is 202° C. and it is similar to that of GBL. Therefore, it is very difficult to remove GBL when fractional distillation is applied directly to the waste NMP mixed solution. However, where GBL reacted with SBH according to the present invention, GBL can be converted into a material having a higher boiling point than NMP and the converted material can be removed by fractional distillation. This can be seen in FIG. 2.

Figure 2:
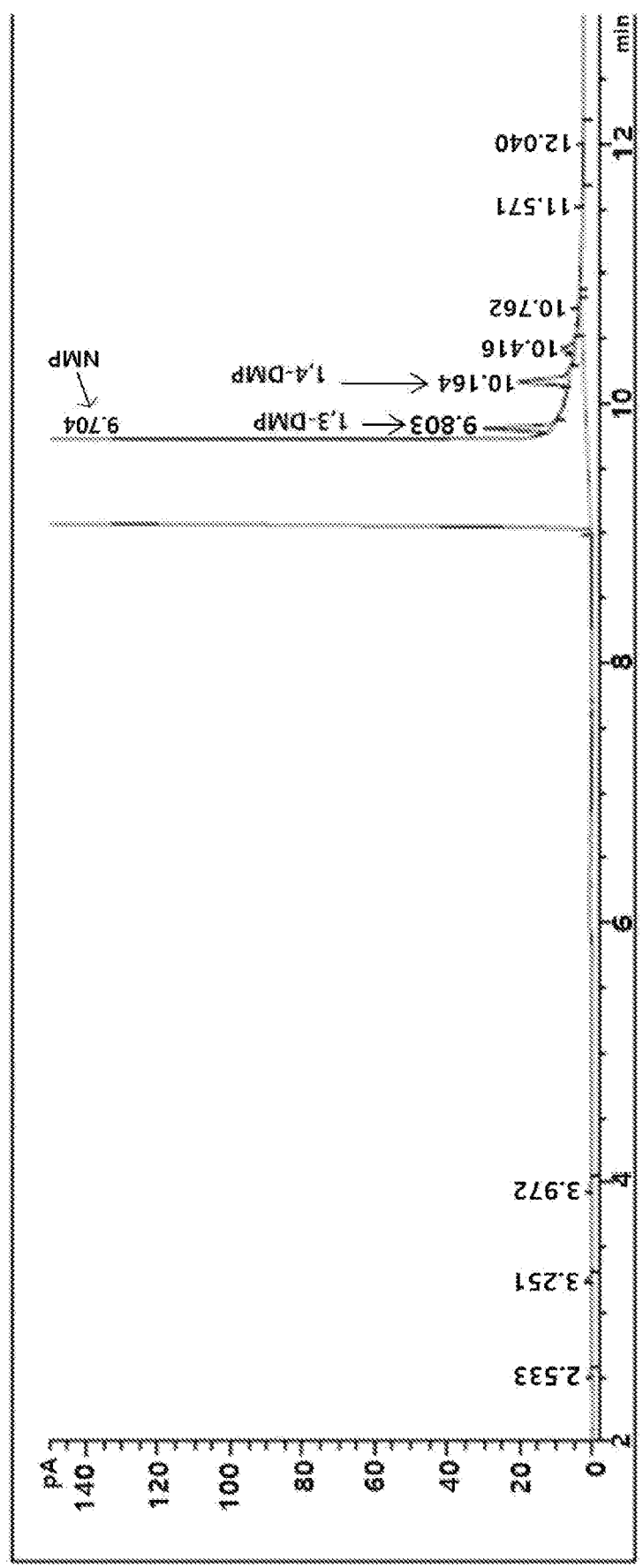
FIG. 2 shows the GC analysis result after SBH treatment with respect to the waste NMP mixed solution.

FIG. 2 shows the GC analysis result after SBH treatment with respect to the waste NMP mixed solution, and peak in GBL or NMS is not observed unlike FIG. 1.

[Reaction Scheme 1]

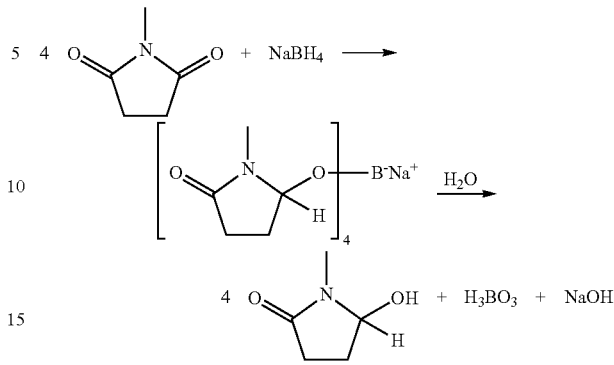

[Reaction Scheme 2]

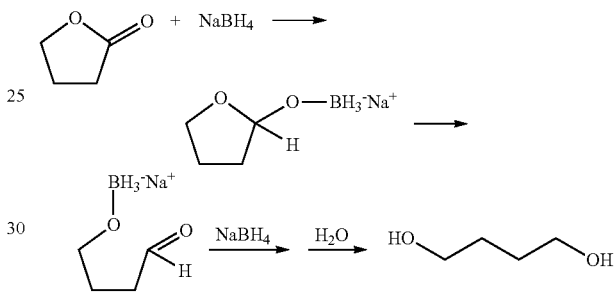

Meanwhile, in the method for purifying a waste NMP mixed solution according to an embodiment of the present invention, the base may be SBH (Sodium Borohydride, $NaBH_4$).

In general, reduction reaction among organic chemical reactions is a reaction combining with hydrogen or lowering the oxidation state. Among the reducing agents that cause this reduction reaction, there are metal hydrides that directly provide hydrogen anions (H—, Hydride). There are typically Lithium Aluminum Hydride (LAH, $LiAlH_4$) and Sodium Borohydride (SBH, $NaBH_4$) as the metal hydrides.

Among the LAH and SBH, LAH has a much stronger reducing power than SBH, and in general, LAH can convert the carbonyl groups of all the following carbonyl (C=O) compounds into methylene ($CH_2$) groups. However, SBH has a weaker reducing power than LAH, so it is generally known that SBH can reduce only ketones in the order of the following compounds.

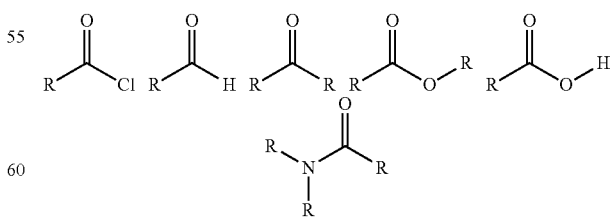

This reduction reaction occurs when the hydride anion attacks C of the carbonyl group, wherein C is partially positive in C=O. From the ester, partial positive electricity of C is weak because O that is next to C of C=O pushes electrons toward C due to the inductive effect, and thus it is known that SBH which has weak reducing power cannot cause a reduction reaction from ester.

However, it seems that in the case of NMS, the reaction takes place easily since NMS has C=O on both sides of the N-methyl group and thus electrons are attracted toward both sides and the partial positive electricity of C of one C=O becomes large, but in the case of NMP, the reaction cannot occur because it has C=O only on one side.

On the other hand, it seems that in the case of GBL, although it is an ester, the reaction proceeds since cyclic ester (Lactone) is more reactive than amide and it becomes a stable structure as the pentagonal structure is released (the strain is relaxed.

In the method for purifying a waste NMP mixed solution according to another embodiment of the present invention, the SBH may be added in an amount of 0.05 to 0.10 wt % based on the total weight of the waste NMP mixed solution. When the amount of SBH added is out of the above range, NMS and GBL contained in the waste NMP mixed solution may not be completely removed at the same time.

In the method for purifying a waste NMP mixed solution according to another embodiment of the present invention, water may be added in an amount of 5 to 20 wt % based on the total weight of the total reactant, the reaction temperature may be 100 to 150° C., and the reaction time may be 10 to 60 minutes. Where the reaction conditions are outside the above range, NMS and GBL contained in the waste NMP mixed solution may not be completely removed at the same time.

In the purification method of the waste NMP mixed solution according to another embodiment of the present invention, the SBH may be dissolved in 10% concentration (w/v) NaOH and added. Where the reaction conditions are outside the above range, NMS and GBL contained in the waste NMP mixed solution may not be completely removed at the same time.

Hereinafter, a method for purifying a waste NMP mixed solution according to an embodiment of the present invention will be described by way of examples. The following examples are presented for illustrative purposes only, and the scope of the present invention is not limited by these examples.

EXAMPLES AND COMPARATIVE EXAMPLES

<Example 1> to <Example 10>

200 g of a waste NMP mixed solution containing NMS and GBL was placed in a 500 mL round bottom flask, wherein the weight of NMS is 200 to 500 wtppm and the weight of GBL is 200 to 400 wtppm based on the total weight of the waste NMP mixed solution. Then, a solution of SBH dissolving in a 10% (w/V) NaOH aqueous solution was added to the waste NMP mixed solution while stirring the waste NMP mixed solution at 200 to 250 rpm at 25 to 150° C. Here, the composition of the waste solution, the amount of SBH input, and the reaction temperature are shown in Table 1 below. In Table 1 below, the amount of SBH input is the amount based on the total weight of the waste mixed solution.

<Comparative Example 1> to <Comparative Example 11>

200 g of waste NMP mixture containing NMS and GBL was added to a 500 mL round bottom flask, wherein the weight of NMS is 200 to 500 wtppm and the weight of GBL is 200 to 400 wtppm based on the total weight of the waste NMP mixed solution. Then, while stirring the waste NMP mixed solution at 25 to 150° C. at 200 to 250 rpm, a 10% (w/v) NaOH aqueous solution was added to the waste NMP mixed solution. Here, the composition of the waste solution, the amount of SBH input, and the reaction temperature are shown in Table 1 below.

As a result of performing the reaction according to Examples 1 to 10 and Comparative Examples 1 to 11, the composition of the waste solution after the reaction is shown in Table 1 below. In Table 1, the content of each component of the waste solution, Comparative Examples and Examples is the content of organic matter excluding water.

TABLE 1

| classification | SBH input (wt %) | Reaction temperature (° C.) | Reaction time (minutes) | GBL (wtppm) | NMP (wt %) | 1,3-DMP (wtppm) | 1,4-DMP (wtppm) | NMS (wtppm) | water (wt %) |
|---|---|---|---|---|---|---|---|---|---|
| Waste solution | — | — | — | 254 | 99.87 | 325 | 344 | 294 | 0.03 |
| Comp.Ex 1 | 0.02 | 25 | 10 | 245 | 99.88 | 327 | 354 | 170 | 0.03 |
| Comp.Ex 2 | 0.05 | 25 | 20 | 168 | 99.89 | 324 | 342 | 160 | 0.03 |
| Comp.Ex 3 | 0.1 | 25 | 30 | 112 | 99.9 | 325 | 340 | 152 | 0.03 |
| Comp.Ex 4 | 0.3 | 25 | 60 | 62 | 99.9 | 323 | 342 | 140 | 0.03 |
| Comp.Ex 5 | 0.02 | 100 | 10 | 238 | 99.89 | 326 | 348 | 152 | 0.03 |
| Comp.Ex 6 | 0.05 | 100 | 20 | 146 | 99.9 | 328 | 340 | 140 | 0.03 |
| Comp.Ex 7 | 0.1 | 100 | 60 | 104 | 99.9 | 320 | 352 | 132 | 0.03 |
| Comp.Ex 8 | 0.05 | 70 | 10 | 112 | 99.91 | 334 | 348 | 62 | 10 |
| Comp.Ex 9 | 0.02 | 100 | 10 | 90 | 99.91 | 322 | 360 | 38 | 10 |
| Comp.Ex 10 | 0.05 | 100 | 5 | 102 | 99.91 | 334 | 351 | 67 | 10 |
| Comp.Ex 11 | 0.05 | 25 | 10 | 83 | 99.91 | 338 | 378 | 104 | 20 |
| Example 1 | 0.05 | 100 | 10 | 0 | 99.92 | 338 | 349 | 0 | 5 |
| Example 2 | 0.1 | 100 | 10 | 0 | 99.92 | 331 | 362 | 0 | 5 |
| Example 3 | 0.05 | 100 | 10 | 0 | 99.92 | 329 | 357 | 0 | 10 |
| Example 4 | 0.05 | 100 | 10 | 0 | 99.92 | 319 | 362 | 0 | 10 |
| Example 5 | 0.05 | 100 | 30 | 0 | 99.92 | 341 | 376 | 0 | 10 |
| Example 6 | 0.05 | 100 | 60 | 0 | 99.92 | 322 | 364 | 0 | 10 |
| Example 7 | 0.1 | 100 | 10 | 0 | 99.92 | 325 | 382 | 0 | 10 |
| Example 8 | 0.05 | 100 | 10 | 0 | 99.92 | 329 | 357 | 0 | 20 |
| Example 9 | 0.1 | 100 | 10 | 0 | 99.92 | 337 | 371 | 0 | 20 |
| Example 10 | 0.05 | 150 | 10 | 0 | 99.92 | 331 | 370 | 0 | 10 |

As can be seen in Table 1, when using waste solution containing about 300 wtppm of NMS and about 250 wtppm of GBL, GBL and NMS remain in the comparative example, whereas GBL and NMS are not observed at all in the examples of the present invention. Therefore, it can be seen that according to the present invention, NMS and GBL can be completely removed from the waste NMP mixed solution at the same time, when the content of SBH is 0.05 to 0.10 wt % under the reaction conditions that content of water is 5 to 20 wt %, a reaction temperature is 100 to 150° C., and a reaction time is 10 to 60 minutes.

In addition, from the results of Comparative Examples 1 to 11 in Table 1, it can be seen that NMS and GBL are not completely removed at the same time from the waste NMP mixed solution where the experimental conditions are out of range of Examples 1 to 10.

Example 11

This is the case where 10% (w/v) aqueous NaOH solution in which SBH was dissolved was treated at a reaction temperature of 100° C. for a waste NMP mixed solution containing 0.12 wt % of NMS and about 270 wtppm of GBL.

<Comparative Example 12> to <Comparative Example 14>

Comparative Examples 12 to 14 are the same as in Example 11, except that a 10% (w/v) aqueous NaOH solution in which SBH is not dissolved was used.

When treating the waste solution according to Example 11 and Comparative Examples 12 to 14, the components of the mixture after treatment are shown in Table 2 below.

11 of the present invention, NMS and GBL in the waste NMP mixed solution were completely removed.

<Example 12> Fractional Distillation Using a Distillation Column

In Examples 7 and 12, the waste NMP mixed solution from which NMS and GBL completely were removed at the same time by applying SBH was fractionated and distilled under a pressure of 40-100 mmHg using a 5 L-scale pilot 30-stage Sieve Tray distillation column to remove 0 to 15% moisture and impurities having a low boiling point, and to recover 15 to 80% of the purified NMP. The results of recovering are shown in Table 3 below. In Table 3 below, the contents of the waste solution and the components of each of the examples are the contents of organic substances excluding water.

TABLE 3

| Example | classification | GBL (wtppm) | NMP (wt %) | 1,3-DMP (wtppm) | 1,4-DMP (wtppm) | NMS (wtppm) | water (wt %) |
|---|---|---|---|---|---|---|---|
| — | Waste solution | 254 | 99.87 | 325 | 344 | 294 | 10 |
| Example 7 | Waste solution (after SBH reaction) | 0 | 99.92 | 325 | 382 | 0 | 10 |
| Example 12 | Waste solution (after SBH reaction and fractional distillation purification) | 0 | 99.92 | 332 | 392 | 0 | 0.03 |

As can be seen in Table 3, in the case of Examples 7 and 12 of the present invention, neither NMS nor GBL existed in the mixture obtained by fractional distillation. Accordingly, it can be seen that impurities such as GBL and NMS can be removed by fractional distillation after treating the waste NMP mixed solution with SBH according to the present invention.

The above description is to simply illustrate the technical scope of the present invention, and various modifications can be made by those skilled in the art without departing from the scope of the essential characteristics of the present invention. Therefore, the embodiments disclosed in the present invention do not intend to limit the present invention, but to explain the present invention, and the scope of the present invention will not be limited by the embodiments. The protective scope of the present invention shall be interpreted as defined in the claims, and all technologies within the scope equivalent thereto should be interpreted as being included in the scope of the present invention.

TABLE 2

| classification | NaOH aq. conc. (%) | SBH input (wt %) | NaOH input (wt %) | Reaction temperature (° C.) | Reaction time (minutes) | GBL (wtppm) | NMP (wt %) | 1,3-DMP (wtppm) | 1,4-DMP (wtppm) | NMS (wtppm) | water (wt %) | pH |
|---|---|---|---|---|---|---|---|---|---|---|---|---|
| Waste solution | — | — | — | — | — | 270 | 99.66 | 323 | 342 | 1200 | 12 | 5.3 |
| Comp.Ex 12 | 10 | 0 | 0.04 | 100 | 10 | 245 | 99.67 | 313 | 341 | 1100 | 12.4 | 6.2 |
| Comp.Ex 13 | 10 | 0 | 0.07 | 100 | 10 | 170 | 99.72 | 326 | 352 | 730 | 12.7 | 7.7 |
| Comp.Ex 14 | 10 | 0.04 | 0.04 | 100 | 10 | 77 | 99.78 | 327 | 352 | 222 | 12.4 | 7.2 |
| Example 11 | 10 | 0.07 | 0.07 | 100 | 10 | 0 | 99.81 | 323 | 388 | 0 | 12.7 | 9.9 |

As can be seen in Table 2, in the case of Comparative Examples 12 and 13, NMS and GBL were hardly removed from the waste solution, and in the case of Comparative Example 14, more NMS and GBL were removed than in Comparative Examples 12 and 13, but were not completely removed. On the other hand, it can be seen that in Example

What is claimed is:

1. A method for purifying waste N-methyl-2-pyrrolidone (NMP) mixed solution comprising N-methylsuccinimide (NMS) and γ-butyrolactone (GBL) being a by-product of NMP, the method comprising:

adding a base comprising $NaBH_4$ (SBH) to the waste NMP mixed solution to perform a reaction of converting the NMS to 5-hydroxy-N-methyl-2-pyrrolidone and converting the GBL to 1,4-butanediol, whereby the NMS and the GBL are simultaneously removed, wherein the SBH is added in an amount of 0.05 to 0.10 wt % based on the total weight of the waste NMP mixed solution, wherein water is added in an amount of 5 to 20 wt % based on the total weight of the NMP mixed solution and the base, a temperature of the reaction is 100 to 150° C., and the reaction is performed for 10 to 60 minutes.

2. The method of claim 1, wherein the SBH is dissolved in 10% concentration (w/v) NaOH and added to the waste NMP mixed solution.

3. The method of claim 1, wherein the 5-hydroxy-N-methyl-2-pyrrolidone is formed by the following reaction scheme 1, and the 1,4-butanediol is formed by the following reaction scheme 2:

[Reaction Scheme 1]

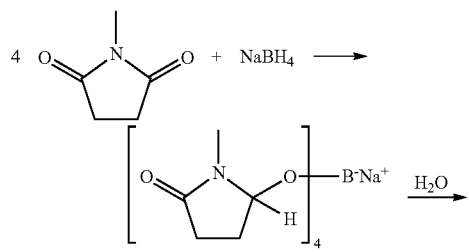

-continued

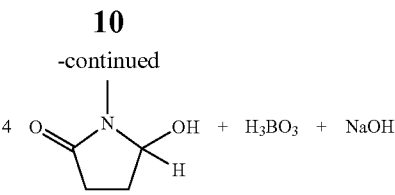

[Reaction Scheme 2]

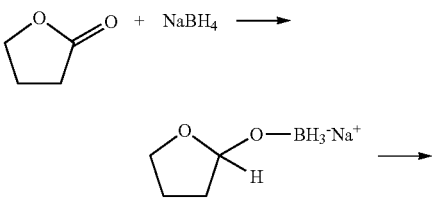

4. The method of claim 1, wherein the waste NMP mixed solution is from a waste solution used in the secondary battery manufacturing process.

* * * * *